United States Patent [19]
Arney

[11] Patent Number: 5,226,888
[45] Date of Patent: Jul. 13, 1993

[54] COILED, PERFUSION BALLOON CATHETER

[76] Inventor: Michelle Arney, 1811 1st Ave. South, Apt. 1, Minneapolis, Minn. 55403

[21] Appl. No.: 782,518

[22] Filed: Oct. 25, 1991

[51] Int. Cl.$^5$ ............................................. A61M 29/00
[52] U.S. Cl. ........................................ 604/96; 604/53; 606/194
[58] Field of Search .................... 604/53, 96–103; 606/191–194

[56] References Cited

U.S. PATENT DOCUMENTS

| | | | |
|---|---|---|---|
| 3,892,519 | 2/1990 | Songer et al. | 604/96 |
| 4,183,102 | 1/1980 | Guiset | 3/1.4 |
| 4,423,725 | 1/1984 | Baran et al. | 128/207.15 |
| 4,581,017 | 4/1986 | Sahota | 604/101 |
| 4,585,000 | 4/1986 | Hershenson | 128/345 |
| 4,661,094 | 4/1987 | Simpson | 604/53 |
| 4,681,564 | 7/1987 | Landreneau | 604/97 |
| 4,762,129 | 8/1988 | Bonzel | 128/344 |
| 4,762,130 | 8/1988 | Fogarty et al. | 606/194 |
| 4,771,777 | 9/1988 | Horzewski et al. | 604/101 X |
| 4,787,388 | 11/1988 | Hofmann | 128/344 |
| 4,790,315 | 12/1988 | Mueller, Jr. et al. | 128/344 |
| 4,795,427 | 1/1989 | Helzel | 604/53 |
| 4,820,271 | 4/1989 | Deutsch | 604/99 |
| 4,850,969 | 7/1989 | Jackson | 604/96 |
| 4,877,031 | 10/1989 | Conway et al. | 128/344 |
| 4,881,939 | 11/1989 | Newman | 600/31 |
| 4,889,137 | 12/1989 | Kolobow | 128/898 |
| 4,901,731 | 2/1990 | Millar | 128/675 |
| 4,909,252 | 3/1990 | Goldberger | 606/194 |
| 4,932,413 | 6/1990 | Shockey et al. | 128/657 |
| 4,944,745 | 7/1990 | Sogard et al. | 606/194 |
| 4,983,167 | 2/1991 | Sahota | 606/194 |
| 5,000,734 | 3/1991 | Boussignac et al. | 604/96 |
| 5,000,743 | 3/1991 | Patel | 606/194 |
| 5,002,531 | 3/1991 | Bonzel | 604/96 |
| 5,078,685 | 1/1992 | Colliver | 604/96 |
| 5,108,370 | 4/1992 | Walinsky | 604/96 |

*Primary Examiner*—C. Fred Rosenbaum
*Assistant Examiner*—Corrine Maglione

[57] ABSTRACT

A perfusion balloon catheter includes an inflatable balloon formed by a series of loops of a flexible, inflatable tube in a generally cooperative tubular shape. The loops are supported by a coiled support member and are locked within the coiled support member by a wire retainer. The cooperative tubular shape of the individual loops perform to provide an inflatable cooperative outer surface of the balloon and a perfusion passage within the balloon.

39 Claims, 8 Drawing Sheets

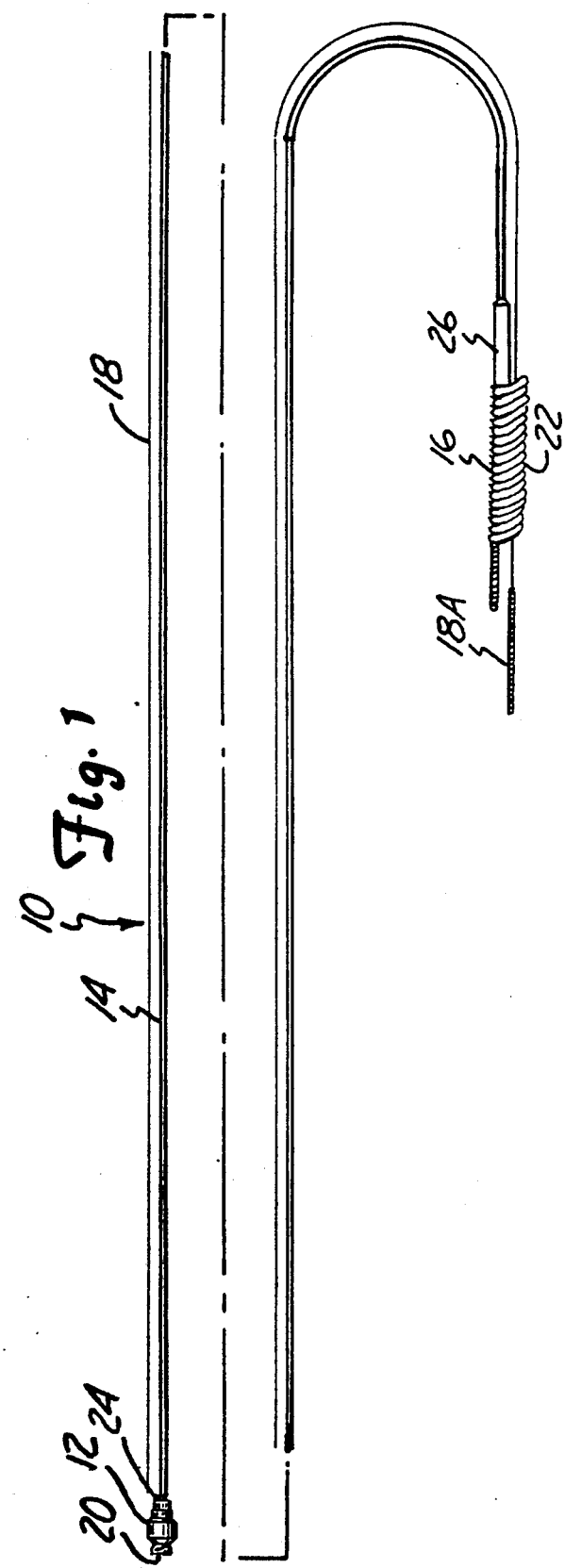

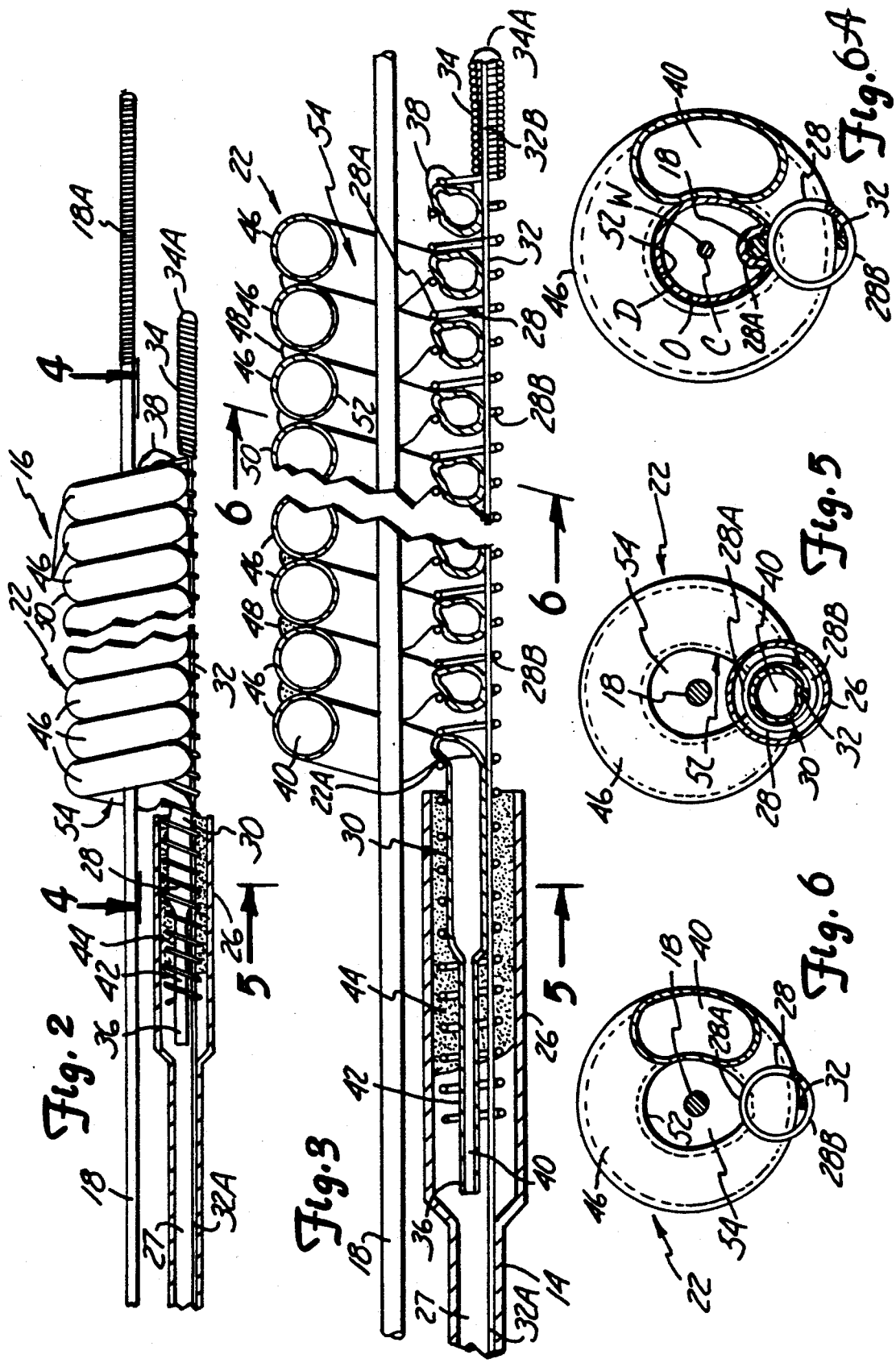

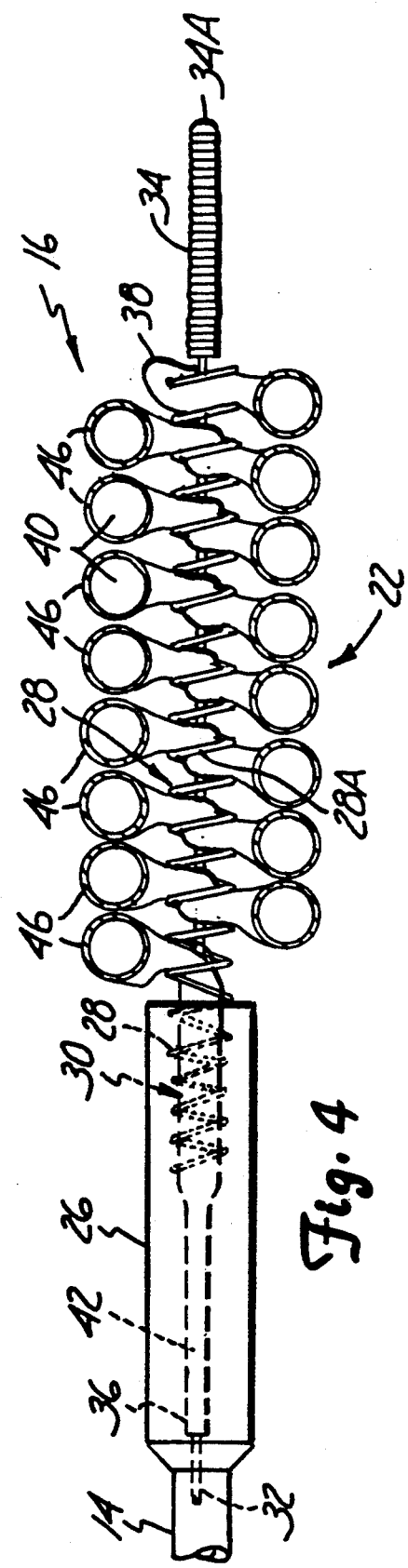

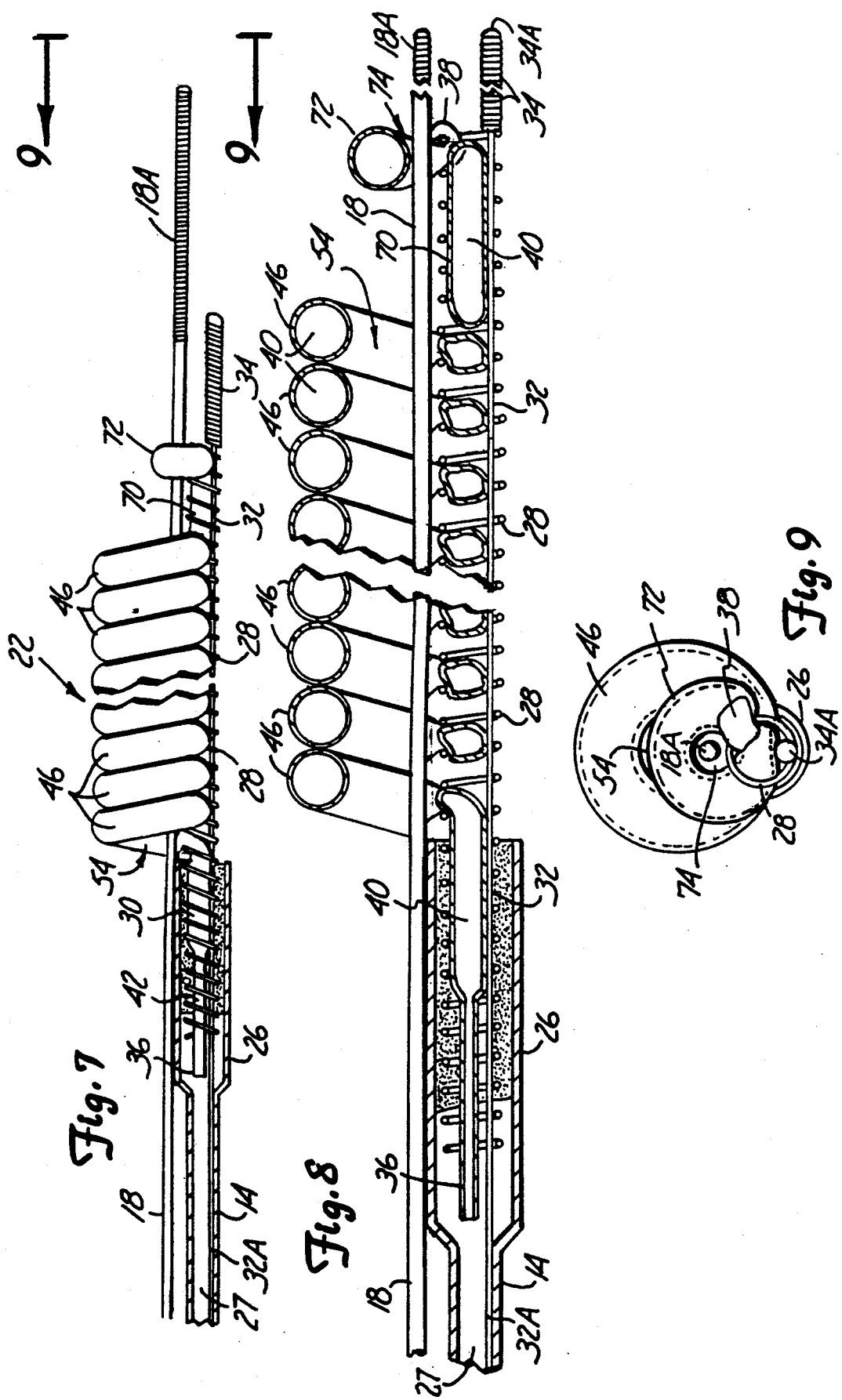

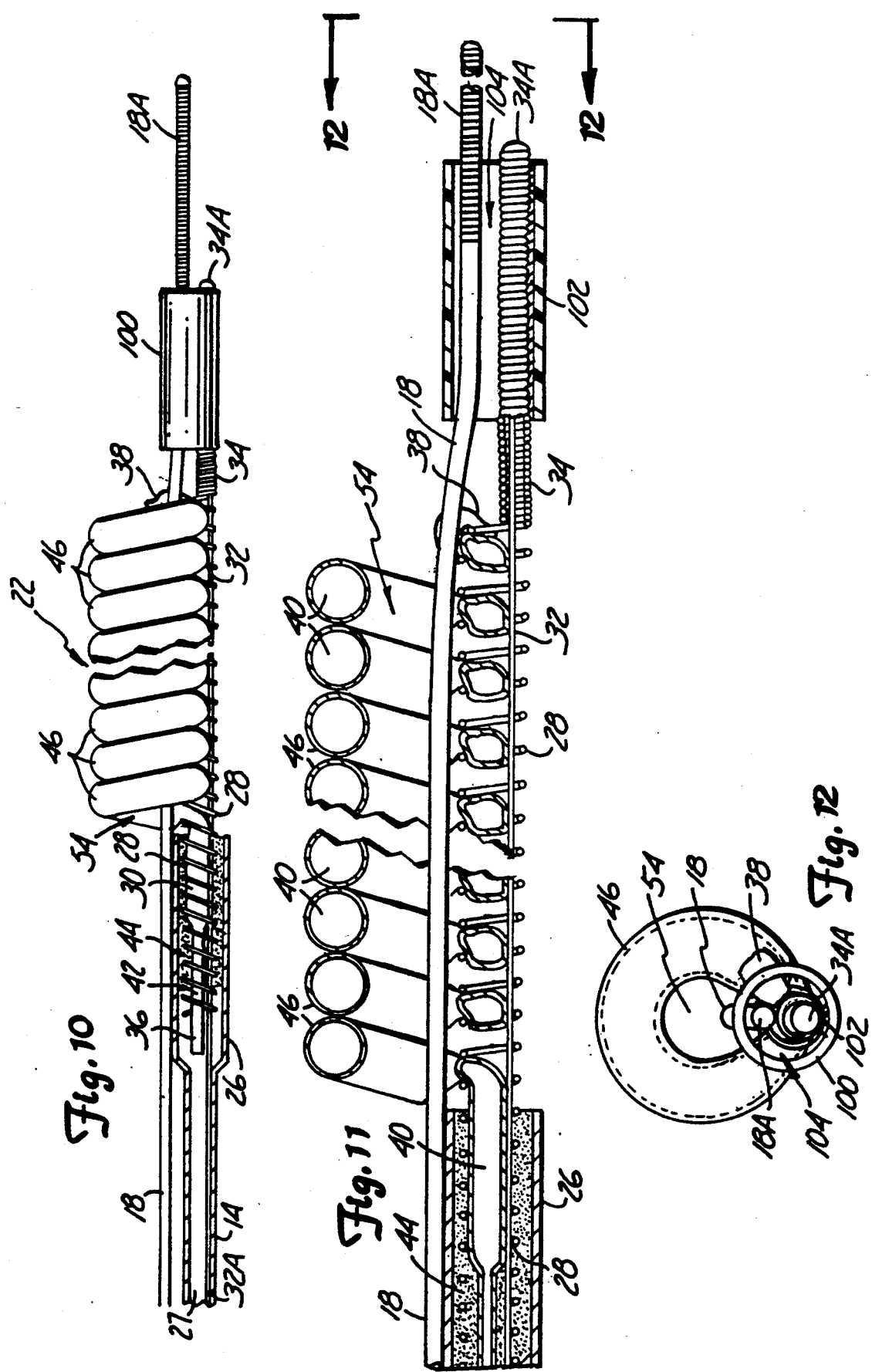

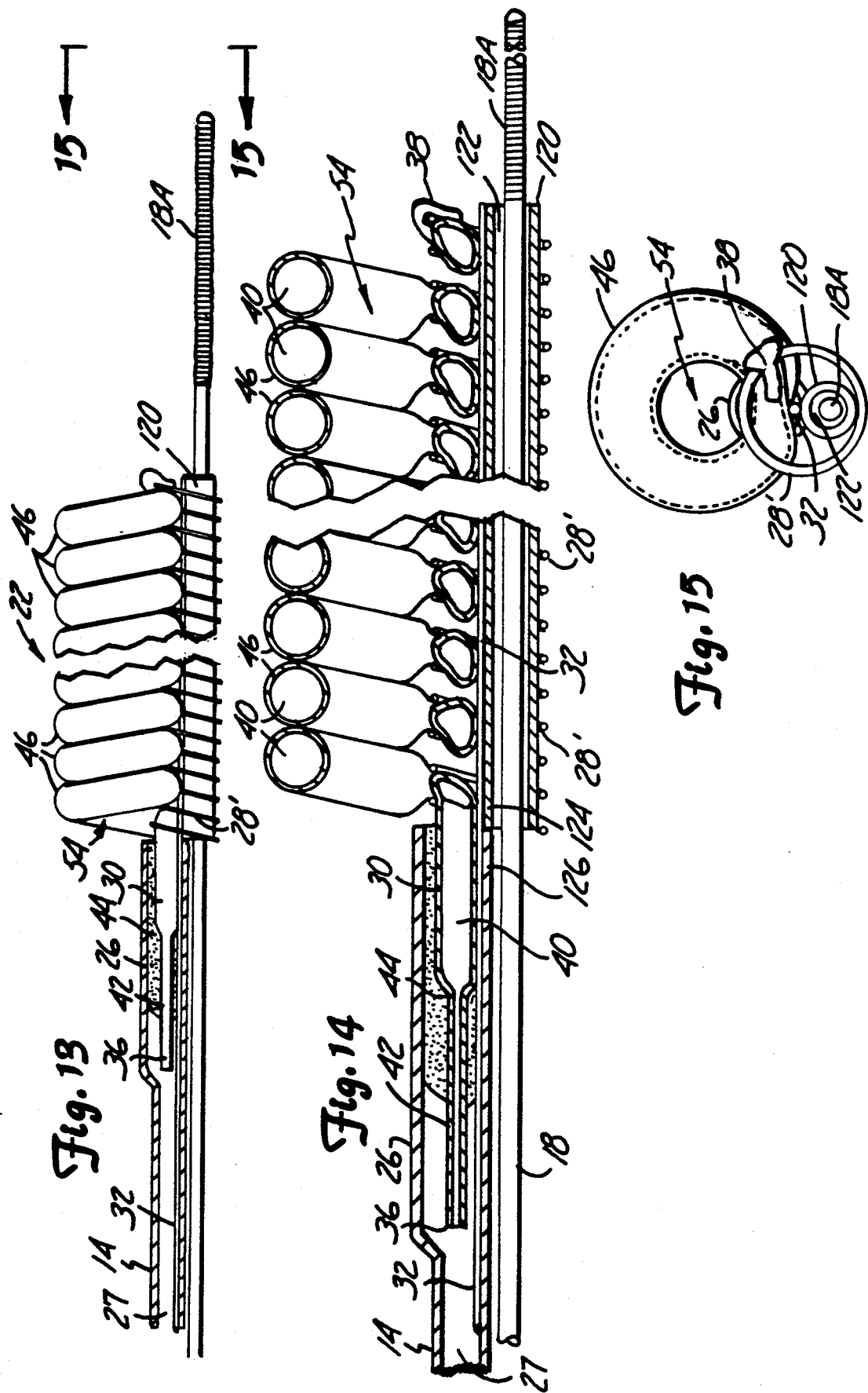

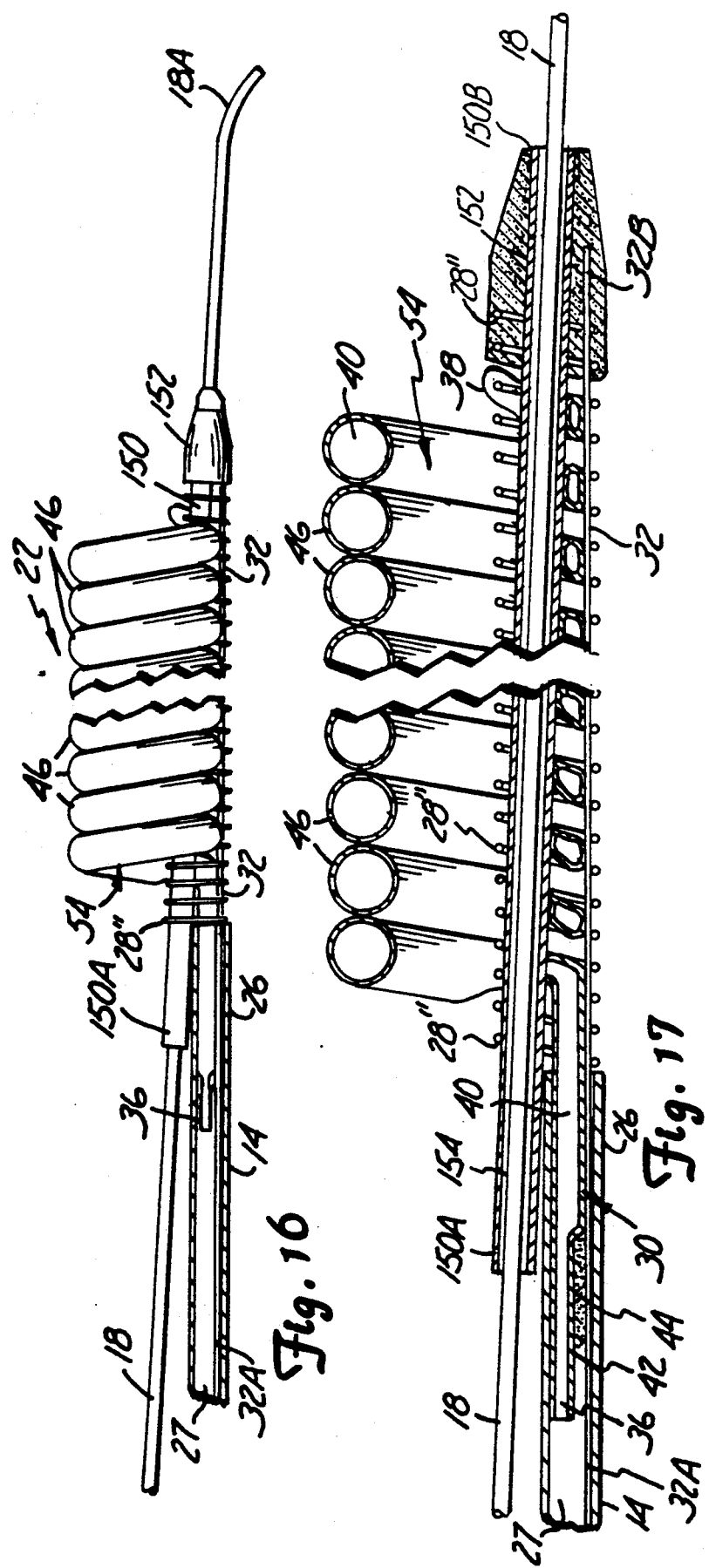

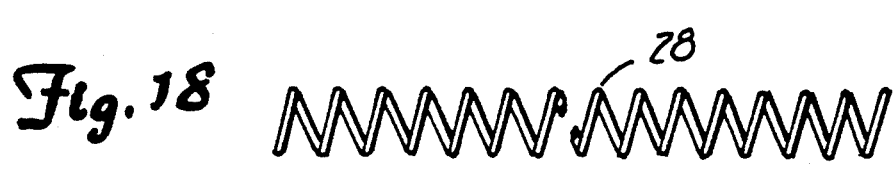
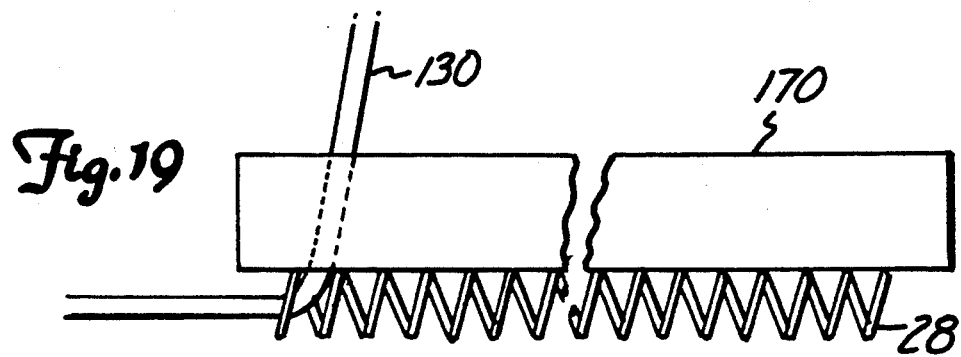
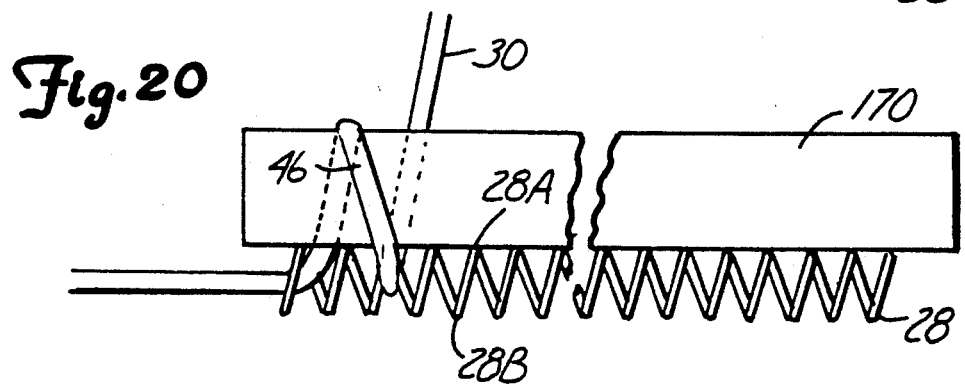
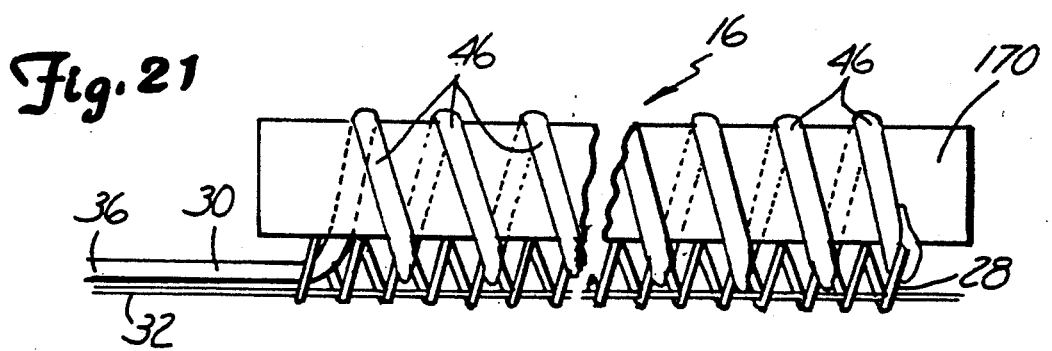
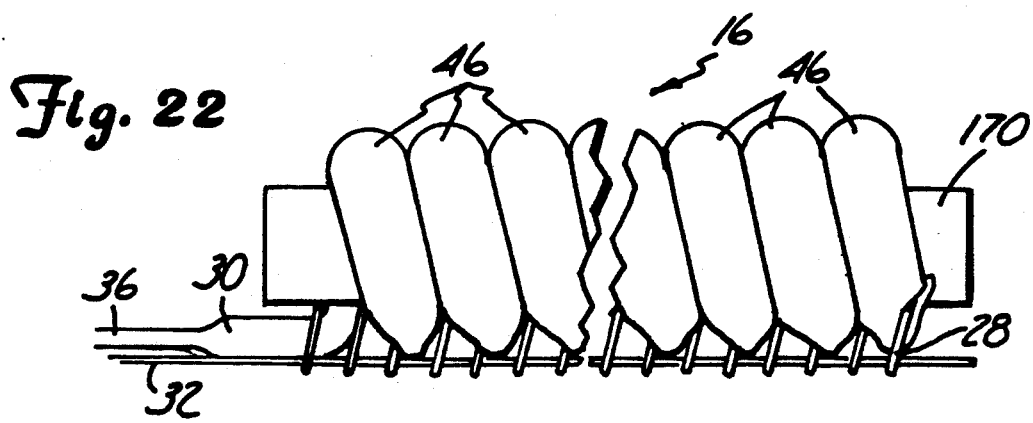

COILED, PERFUSION BALLOON CATHETER

BACKGROUND OF THE INVENTION

The present invention relates to the field of angioplasty. In particular, the present invention relates to a balloon catheter which permits prolonged inflation of the balloon within a blood vessel, such as a coronary artery, without blocking blood flow by utilizing passive perfusion.

Angioplasty has gained wide acceptance as an efficient, effective and alternative method of treating constrictions caused by undesirous tissue growth or lesions on the inner walls of the blood vessels. Such tissue growth or lesions cause a narrowing of the blood vessels called a "stenosis" which severely restricts or limits the flow of blood. In the most widely used form of angioplasty, a dilatation catheter, which has an inflatable balloon at its distal end, is guided through the vascular system. With the aid of fluoroscopy, a physician is able to position the balloon across the stenosis. The balloon is then inflated by applying fluid pressure through an inflation lumen of the catheter to the balloon. Inflation of the balloon stretches the artery and presses the stenosis-causing lesion into the artery wall to remove the constriction and re-establish acceptable blood flow through the artery.

One disadvantage of many balloon catheters of the prior art is the complete occlusion of the blood vessel that results while the balloon is inflated. Prolonged complete blockage of a blood vessel poses serious risk of damage to the tissue, downstream from the occlusion, which is deprived of oxygenated blood. This consequence poses a severe limitation on the length of time the balloon can remain expanded within an artery to effectively treat the stenosis. Longer inflation times increase the probability that the artery will remain open after the catheter is removed.

Various methods for providing passive perfusion of blood through or past the inflated balloon are found in the following prior art references: Guiset U.S. Pat. No. 4,183,102; Baran et al. U.S. Pat. No. 4,423,725; Sahota U.S. Pat. No. 4,581,017; Hershenson U.S. Pat. No. 4,585,000; Horzewski et al. U.S. Pat. No. 4,771,777; Mueller et al. U.S. Pat. No. 4,790,315; Songer et al. U.S. Pat. No. 4,892,519; Goldberger U.S. Pat. No. 4,909,252; Sogard et al. U.S. Pat. No. 4,944,745; Sahota U.S. Pat. No. 4,983,167 and European patent application 0 246 998; Boussignac et al. U.S. Pat. No. 5,000,734; Patel U.S. Pat. No. 5,000,743; and Bonzel U.S. Pat. No. 5,002,531.

A disadvantage of prior tubular-shaped, perfusion balloon catheters is the additional manufacturing steps necessary to connect outer and inner skins of the balloon to create a perfusion passage between the upstream side of the balloon and the down-stream side of the balloon. Another disadvantage is the risk of interrupted integrity of the balloon at the seams created by the connection of outer and inner skins. Additionally, tubular-shaped balloons of the prior art are relatively stiff due to the seams and internal support structures. There is still a need in the field, therefore, for a balloon catheter with good flexibility and a perfusion cavity which, when inflated within an artery, permits good arterial blood flow, and yet is capable of being manufactured with relative ease and minimal cost.

SUMMARY OF THE INVENTION

The present invention is a perfusion balloon catheter which includes a shaft with a shaft lumen, a support structure which extends distally from a distal end of the shaft, and a balloon formed by a flexible, inflatable tube carried by the support structure. The perfusion balloon catheter of the present invention uses a coiled support member, as the support structure, to hold a series of adjacent loops of the flexible tube and thereby form a composite balloon having a tubular shape. A distal end of the coiled, flexible tube is sealed, and a proximal end of the flexible tube is in fluid communication with the shaft lumen.

The balloon formed by the tube loops, when inflated, has an outer surface which interacts with the wall of the artery, and an inner surface which defines a passive perfusion passage. The present invention permits prolonged inflation of the balloon during a dilatation procedure while reducing the risk of tissue damage distal to the balloon location.

BRIEF DESCRIPTION OF THE DRAWINGS

FIG. 1 is a side view of a first embodiment of the perfusion balloon catheter of the present invention.

FIG. 2 is a side view, partially in section, of the distal end of the catheter of FIG. 1.

FIG. 3 is a longitudinal sectional view of the balloon assembly.

FIG. 4 is a sectional view of the balloon assembly taken along line 4—4 of FIG. 2.

FIG. 5 is a cross sectional view of the balloon assembly taken along line 5—5 of FIG. 3.

FIG. 6 is a cross sectional view of the balloon assembly taken along line 6—6 of FIG. 3.

FIG. 6A is a view of the balloon assembly of FIG. 6 shown with a dilatation balloon.

FIG. 7 is an enlarged side view, partially in section, of a second embodiment of the present invention.

FIG. 8 is a longitudinal sectional view of the balloon assembly of FIG. 7.

FIG. 9 is an end view of the balloon assembly taken from line 9—9 of FIG. 7.

FIG. 10 is a side view, partially in section, of a third embodiment of the present invention.

FIG. 11 is a longitudinal sectional view of the balloon assembly shown in FIG. 10.

FIG. 12 is an end view of the balloon assembly taken from line 12—12 of FIG. 10.

FIG. 13 is an enlarged side view, partially in section, of a fourth embodiment of the present invention.

FIG. 14 is a longitudinal sectional view of the balloon assembly of FIG. 13.

FIG. 15 is an end view of the balloon assembly taken along line 15—15 of FIG. 13.

FIG. 16 is an enlarged side view, partially in section, of a fifth embodiment of the present invention.

FIG. 17 is a longitudinal sectional view of the balloon assembly of FIG. 16.

FIG. 18 is a side view of the coiled support member of the balloon assembly.

FIG. 19 is an enlarged side view of the coiled support member, mandril and initial position of the flexible tube.

FIG. 20 is a side view of the coiled support member, mandril, and flexible tube looped once around the coiled support member and mandril.

FIG. 21 is a side view of the coiled support member, mandril, and series of loops of the flexible tube around the coiled support member and mandril.

FIG. 22 is a side view of the coiled support member, mandril, and tube loops with the flexible tube inflated.

DETAILED DESCRIPTION OF THE PREFERRED EMBODIMENTS

1. The First Embodiment (FIGS. 1-6)

FIG. 1 shows a side view of perfusion balloon catheter 10, which includes manifold 12, elongated tubular shaft 14, balloon assembly 16, and guide wire 18.

Manifold 12 is located at the proximal end of catheter 10. Manifold 12 includes inflation port 20, through which inflation fluid is provided to and withdrawn from inflatable multiple-loop composite balloon 22 of balloon assembly 16.

Elongated tubular shaft 14 of catheter 10 is a single lumen tube having its proximal end 24 connected to manifold 12 and its distal end 26 connected to balloon 22 of balloon assembly 16. Shaft lumen 27 (shown in FIG. 2), which extends through shaft 14 from proximal end 24 to distal end 26, is in fluid communication with inflation fluid port 20 of manifold 12, and also with balloon 22 of balloon assembly 16.

In preferred embodiments, shaft 14 possesses the qualities of compression rigidity along the longitudinal axis, which facilitates advancement of catheter 10 through the vascular system, and good distal flexibility, which enhances maneuverability of catheter 10 through directional changes of the vascular system. These qualities are achievable in a variety of ways. In one embodiment, the proximal region of shaft 14 is a stainless steel hypo tube, and the distal region is a polyethylene tube which is connected to the proximal region. In another embodiment, shaft 14 is formed from a single piece of polymer tubing with a proximal region that has an outer and inner diameter larger than an outer and inner diameter of a distal region.

Guide wire 18 is external to and proximate to shaft 14 and runs the entire length of catheter 10. Guide wire 18 ends, at its distal end, with guide wire spring tip 18A. Catheter 10 is movable longitudinally over guide wire 18.

In FIG. 2, an enlarged side view of distal end 26 of shaft 14 and balloon assembly 16 is shown. Balloon assembly 16 includes coiled support member 28, inflatable tube 30 (which forms balloon 22) and retainer 32.

Coiled support member 28 has its proximal end mounted within flared distal end 26 of shaft 14 and extends distally from distal end 26. Adjacent coils of coiled support member 28 are spaced apart to hold tube 30 in a looped configuration along coiled support member 28. The distal end of coiled support member 28 terminates in a series of reduced diameter tight coils which form spring tip 34 of catheter 10. Coiled support member 28 is made of any flexible material capable of being formed into a coil, such as a metal wire or ribbon. Alternatively, other open support structures, such as an open-braided/strand-woven tube, can also hold tube 30 in a looped configuration.

Flexible tube 30 is a flexible, inflatable polyolefin copolymer material, such as Surlyn 8527 from Dupont, and cooperates with coiled support member 28 to form balloon 22. As shown in FIGS. 2-4, proximal end 36 of flexible tube 30 is located within flared distal end 26 of shaft 14. Distal end 38 of flexible tube 30 is sealed and is located near the distal end of coiled support member 28. Tube lumen 40 extends through tube 30 from proximal end 36 to distal end 38.

Proximal neck region 42 of flexible tube 30 is located within flared distal end 26, and has a smaller outer diameter and larger wall thickness than the remainder of tube 30. Tube 30 extends through the longitudinal interior of coiled support member 28 until tube 30 passes out of flared distal end 26 of shaft 14. Adhesive 44 fills a portion of the cavity within flared distal end 26 to attach the proximal portions of coiled support member 28, tube 30 and retainer 32 to shaft 14.

In the embodiment shown in FIGS. 2-6, the portion of tube 30 which extends distally out of flared distal end 26 is threaded between every other coil of coiled support member 28 and passes under upper extent 28A of every other coil of coiled support member 28 to form a series of inflatable, side-by-side loops 46. When inflation fluid from shaft lumen 27 is supplied to tube lumen 40, loops 46 inflate and cooperate to form balloon 22 (as illustrated in FIGS. 2-6).

Loops 46 are captured within coiled support member 28 by retainer 32. Retainer 32 is preferably a wire which extends from shaft 14 through coiled support member 28 and spring tip 34. Proximal end 32A of retainer 32 lies within shaft 14 and extends proximal to flared distal end 26 to shaft 14. Distal end 32B of retainer 32 is attached to distal end 34A of spring tip 34. Retainer 32 is positioned between the bottom of each loop 46 and lower extents 28B of the coils of coiled support member 28. Loops 46, therefore, are captured between retainer 32 and upper extents 28A of the coils. Retainer 32 thus serves to retain each tube loop 46 in a fixed position along coiled support member 28 while providing structural support to balloon assembly 16 at the distal end of catheter 10.

In order to ensure that loops 46 act as a unit, the tops of loops 46 are connected together by adhesive 48. Alternatively, loops 46 can be fixed together by applying a flexible coating over loops 46. The plurality of tube loops 46 define a generally tubular shaped balloon 22 having a composite outer surface 50 and a composite inner surface 52. Outer surface 50 applies a radially outward force to an artery wall when balloon 22 is inflated. Inner surface 52 defines perfusion passage 54 which extends through the length of balloon 22.

As shown in FIG. 6A, dilatation balloon D is coincidentally disposed at distal end 26 of shaft 14, within the perfusion passage 54 to enhance the radial outward force of outer surface 50. Dilatation balloon D (which is similar to a balloon of a dilatation balloon catheter shown in U.S. Pat. No. 4,943,278) has outer surface O, core wire W and inner cavity C which is in fluid communication with lumen 27 of shaft 14. Alternatively, dilatation balloon D can be disposed at a distal end of a catheter shaft which has separate inflation lumens, or at a distal end of a second catheter shaft. Dilatation balloon D is inflated with balloon 22 such that outer surface O of dilatation balloon D contacts inner surface 52 of perfusion passage 54, causing an outward radial force of dilatation balloon D to be transmitted to composite outer surface 50 of balloon 22. With the artery wall expanded by the composite outward radial force of balloon 22 and dilatation balloon D, dilatation balloon D is deflated to permit the flow of blood through perfusion passage 54 while balloon 22 remains inflated within the artery. Alternatively, dilatation balloon D may be moved proximal to balloon 22 to permit the flow of blood through perfusion passage 54.

The cross-sectional area of perfusion passage 54, which ranges from about 16 to about 44 percent of the cross-sectional area of composite outer surface 50, permits a flow of blood through balloon 22 while balloon 22 is inflated within the artery. Perfusion passage 54 is large enough to coincidentally serve as a guide passage for guide wire 18. Because balloon 22 is very short compared to the total lengths of catheter 10 and guide wire 18, the use of perfusion passage 54 as a guide passage permits rapid exchange of catheter 10 over guide wire 18 while guide wire 18 remains in place in the artery with the distal end of guide wire 18 in position across the stenosis.

FIG. 5 shows a cross-sectional view of a proximal portion of balloon assembly 16. For purposes of illustration, adhesive 44 is not shown in FIG. 5. Coiled support member 28 is shown within flared distal end 26. Flexible tube 30 is positioned within coiled support member 28. Retainer 32 is positioned below tube 30 and between coiled support member 28 and tube 30.

As illustrated in both FIGS. 5 and 6, inner surface 52 of loop 46 defines perfusion passage 54, which also serves as a guide passage for guide wire 18. Guide wire 18 has an unrestricted range of motion within the entire perfusion passage 54. Perfusion passage 54 readily provides an avenue for blood flow during a dilatation procedure while coincidentally serving as a passage for guide wire 18.

Catheter 10 shown in FIGS. 1-6A is capable of being used with guide wire 18 (over-the-wire rapid exchange use) or without guide wire 18 (stand-alone use as a fixed wire catheter). Without guide wire 18, spring tip 34 permits use of catheter 10 as a fixed wire catheter.

2. The Second Embodiment (FIGS. 7-9)

FIGS. 7-9 show a second embodiment of the present invention which is generally similar to the first embodiment shown in FIGS. 1-6. Similar reference characters are used to designate similar elements.

This second embodiment differs from the first embodiment in that distal region 70 of flexible tube 30 transitions back within coiled support member 28 at the distal end of balloon 22. Coiled support member 28 extends distally beyond balloon 22, as shown in FIGS. 7 and 8. Distal region 70 of tube 30 extends distally through the longitudinal interior of several coils of coiled support member 28, and then extends out coiled support member 28 to form guide loop 72 at the distal end of coiled support member 28. Distal end 38 of tube 30 is bound to a distal-most coil of coiled support member 28 to seal the distal end of tube lumen 40.

Guide loop 72 has inner and outer diameters which are smaller than the inner and outer diameters of loops 46 of balloon 22. Guide loop 72 defines distal guide passage 74 for guide wire 18.

Distal guide passage 74 is generally aligned with perfusion passage 54 of balloon 22. Guide wire 18 extends through perfusion passage 54 and distal guide passage 74 and out the distal end of guide loop 72. The reduced dimensions of guide loop 72 relative to loops 46 restricts the range of transverse movement of guide wire 18 and directs guide wire 18 closer to catheter spring tip 34.

3. The Third Embodiment (FIGS. 10-12)

FIGS. 10-12 show a third embodiment of the present invention. This third embodiment is similar to the embodiment shown in FIGS. 1-6 except that catheter spring tip 34 is extended and guide wire support sleeve 100 is mounted on spring tip 34. In FIGS. 10-12, reference characters similar to those used in FIGS. 1-6 are used to designate similar elements.

Guide wire support sleeve 100 is positioned over spring tip 34 with the distal end of guide wire support sleeve 100 generally aligned with distal end 34A of spring tip 34. An inner surface of guide wire support sleeve 100 is bonded by adhesive 102 to spring tip 34. Guide passage 104 of sleeve 100 is located distally of perfusion passage 54. Guide wire 18 extends through perfusion passage 54 and guide passage 104 and out the distal end of guide wire support sleeve 100.

4. The Fourth Embodiment (FIGS. 13-15)

FIGS. 13-15 show a fourth embodiment of the present invention. This embodiment differs from previous embodiments primarily by virtue of guide wire tube 120, which extends from distal end 26 of shaft 14 through coiled support member 28'. Coiled support member 28', therefore, is larger in diameter than coiled support member 28 of the previous embodiments.

Flexible tube 30 is made of a flexible tubular material and cooperates with coiled support member 28' to form balloon 22. Flexible tube 30 includes proximal neck region 42, which is bonded within distal end 26 of shaft 14 by adhesive 44. Tube lumen 40 of flexible tube 30 is in fluid communication with shaft lumen 27.

Flexible tube 30 extends out of distal end 26 and into coiled support member 28'. Tube 30 forms a plurality of inflatable loops 46 which are held in place between coiled support member 28' and retainer 32. Loops 46 cooperate to form inflatable balloon 22.

Guide wire tube 120 has a length approximately equal to the length of coiled support member 28', and is positioned within coiled support member 28' below tube 30 and adjacent to retainer 32. The lower outer surface of guide wire support tube 120 contacts the lower inner surface of coiled support member 28'. Guide wire tube 120 and retainer 32 are maintained within coiled support member 28' by a bonding material, such as epoxy. The inner diameter of guide wire tube 120 defines guide wire lumen 122 for passage of guide wire 18.

The proximal end of coiled support member 28' is adjacent to flared distal end 26 of catheter shaft 14. The proximal end of guide wire tube 120 generally abuts flared distal end 26, with an upper internal surface 124 of guide wire tube 120 generally aligned with a lower external surface 126 of flared distal end 26. The proximal end of guide wire tube 120 therefore provides access for guide wire 18 external to catheter shaft 14. The location of guide wire tube 120 distal and external to catheter shaft 14 permits a physician performing a dilatation procedure to make a rapid catheter exchange of one size perfusion balloon catheter for another.

In this particular embodiment, a separate catheter spring tip (like tips 34 of the first three embodiments) is not used. The catheter of FIGS. 13-15 is intended for over-the-wire use, and a separate spring tip is not required.

5. The Fifth Embodiment (FIGS. 16 and 17)

FIGS. 16 and 17 show a fifth embodiment of the present invention. This embodiment differs from the other embodiments primarily by virtue of guide wire tube 150, and distal end adhesive 152.

As shown in FIGS. 16 and 17, guide wire tube 150 is positioned primarily within coiled support member 28". Proximal end 150A of tube 150 is located adjacent distal end 26 of shaft 14 and proximal to the proximal end of coiled support member 28". Tube 150 extends distally beyond the distal end of coiled support member 28". Tube 150 defines guide lumen 154 for guide wire 18.

Loops 46 of tube 30, which form balloon 22, are captured at their lower extremes between tube 150 and retainer 32. Retainer 32 extends from within shaft 14, through coiled support member 28" and into distal end guide 152. Retainer 32 is positioned adjacent to and above lower extents 28B of each coil of coiled support member 28".

Distal end adhesive 152 is disposed on distal end 150B of guide wire tube 150, distal end 32B of retainer 32 and the distal end of coiled support member 28" to secure tube 150, retainer 32 and coiled support member 28" at the distal end of catheter 10. The distal end of adhesive 152 is aligned with distal end 150B and is generally tapered from its proximal to its distal end to provide a streamlined profile of the distal end of catheter 10.

The balloon assembly shown in FIGS. 16 and 17 is bonded within distal end 26 of shaft 14. Proximal neck region 42 of tube 30 and proximal end 32A of retainer 32 are inserted within shaft lumen 27 at distal end 26 of shaft 14 with the proximal end of coiled support member 28" generally abutting distal end 26 of shaft 14. Retainer 32 extends into shaft lumen 27 of shaft 14 a distance greater than tube 30 and serves to support balloon assembly 16 and provide distal shaft pushability. Proximal neck region 42 and proximal end 32A of retainer 32 are bonded within distal end 26 of shaft 14 by adhesive 44. Lumen 40 of flexible tube 30 is in fluid communication with shaft lumen 27 and provides a means for inflating and deflating loops 46 of balloon 22.

Proximal end 150A of guide wire tube 150 is positioned adjacent to and above distal end 26 of shaft 26 upon installation of the balloon assembly 16 onto shaft 26. In a preferred embodiment, proximal end 150A and distal end 26 are bonded together (e.g., by an adhesive) in the piggyback configuration shown in FIGS. 16 and 17.

6. The Method of Manufacture (FIGS. 18-22)

FIGS. 18-22 show the components and the steps necessary to manufacture balloon assembly 16 of the embodiments shown in FIGS. 1-12. For purposes of this description, the method of manufacture will be described as proceeding from the proximal to the distal end of coiled support member 28.

As shown in FIGS. 18-22, an uninflated length of flexible tube 30 is inserted at the proximal end of coiled support member 28. Mandril 170 is positioned above and adjacent to the outer surface of coiled support member 28. Tube 30 is threaded through a side of coiled support member 28 as shown in FIG. 19. Tube 30 is wrapped in a distal direction around mandril 170 and coiled support member 28, and threaded between adjacent coils of coiled support member 28. Slight tension is then applied to tube 30 to secure tube 30 under upper extent 28A of a coil of coiled support member 28. Tube 30 is repeatedly looped in the fashion just described to form a series of inflatable, side-by-side loops 46. While FIG. 21 shows tube 30 passing between every other coil of coiled support member 28, spacings of tube 30 may vary depending on the size of the tubing or the coiled support member used. The distal end of tube 30 is then secured to the distal end of coiled support member 28 to seal distal end 38 of tube 30. Retainer 32 is then threaded through the length of coiled support member 28 between the bottom side of each tube loop 46 and lower extents 28B to lock tube loops 46 within coiled support member 28.

With mandril 170 in place, tube 30 is heated to about 80° Celsius for about thirty seconds. Air pressure is applied to the open proximal end 36 of tube to cause tube 30 and loops 46 to inflate and expand the outer diameter of tube 30. Tube 30 is then cooled in a room-temperature water bath, the air pressure is removed, and the support mandril 170 is removed. Balloon assembly 16 is then disposed at the distal end of catheter shaft 14 (not shown) according to the methods shown for the various embodiments in FIGS. 1-17.

Balloon assembly 16 of the embodiment shown in FIGS. 13-15 is manufactured similar to the embodiments shown in FIGS. 1-12 with one exception: the placement and location of guide wire tube 120 within coiled support member 28' succeeds placement of retainer 32.

Balloon assembly 16 of the embodiment shown in FIGS. 16-17 is also manufactured similar to the embodiments shown in FIGS. 1-12, except the location and placement of guide wire tube 150 within coiled support member 28" precedes the wrapping of tube 30 around mandril 170 and coiled support member 28". Loops 46 of tube 30 are therefore secured beneath guide wire tube 150.

7. Conclusion

The perfusion balloon of the present invention is simply constructed at an efficient manufacturing cost. The helical tube creates a generally tubular-shaped perfusion balloon which, unlike prior art tubular-shaped perfusion balloons, requires no additional intra-cavity structural support to create and maintain the perfusion passage during balloon inflation. In addition, the perfusion balloon of the present invention has fewer seams than previous tubular-shaped perfusion balloons which increases flexibility of the distal end of the catheter. Finally, the perfusion balloon of the present invention possesses a perfusion passage with a cross-sectional area which is between about 16 to 44 percent of the cross-sectional area of the inflated balloon. This permits the perfusion balloon of the present invention to remain inflated within the artery while allowing good blood flow through the perfusion passage.

While use of a dilatation balloon with a perfusion balloon catheter of the present invention has been described only with reference to the first embodiment, such use is incorporated by reference to embodiments 2 through 5. Additionally, as well known in the art, radiopaque material is incorporated into each embodiment of the present invention as a marker to permit a physician to monitor the advancement and positioning of the catheter.

Although the present invention has been described with reference to preferred embodiments, workers skilled in the art will recognize that changes may be made in form and detail without departing from the spirit and scope of the invention.

What is claimed is:

1. A perfusion balloon catheter comprising:
   an elongated tubular shaft having a proximal end, a distal end and a lumen extending therethrough;
   a helical coil of flexible, inflatable tube disposed at the distal end of the tubular shaft, the tube having a proximal end in fluid communication with the lumen and having a sealed distal end, the helical coil forming a composite outer surface and composite inner surface which define an inflatable tubular-shaped balloon, the composite inner surface further defining a perfusion passage;
   a longitudinally-extending support structure through which the tube is looped to form the balloon; and
   retainer means for securing the tube to the support structure.

2. The perfusion balloon catheter of claim 1 wherein the support structure is a coiled support member.

3. The perfusion balloon catheter of claim 2 wherein the retainer means includes a wire which extends through the coiled support member to capture loops of the tube in the coiled support member.

4. The perfusion balloon catheter of claim 3 wherein a first length of tube is inside the coiled support member.

5. The perfusion balloon catheter of claim 4 wherein the proximal end of the tube is positioned within the shaft lumen.

6. The perfusion balloon catheter of claim 5 wherein a second length of the tube extends outside of the coiled support member and is looped around the coiled support member to form a plurality of adjacent loops which cooperate to form the inflatable balloon.

7. The perfusion balloon catheter of claim 6 wherein the tubular-shaped balloon has an inner diameter which is larger than an outer diameter of the coiled support member thereby forming the perfusion passage, which extends from a proximal end to a distal end of the balloon.

8. The perfusion balloon catheter of claim 7 and further comprising means for connecting adjacent loops of the tubular-shaped balloon.

9. The perfusion balloon catheter of claim 7 wherein the perfusion passage has an opening, upon inflation of the balloon, with a cross-sectional area of greater than about 15 percent of a total cross-sectional area of the opening and the balloon.

10. The perfusion balloon catheter of claim 2 wherein the retainer means is positioned between each loop of the tube and an inner surface of the coiled support member.

11. The perfusion balloon catheter of claim 2 wherein the tubular shaft includes an outer surface, an inner surface and an opening at the distal end of the shaft and wherein the coiled support member includes an outer surface and a proximal end, the opening and the inner surface of the distal end of the tubular shaft conformably accepting the outer surface of the proximal end of the coiled support member, the proximal end of the coiled support member bonded within the distal end of the tubular shaft.

12. A perfusion balloon catheter comprising:
    an elongated tubular shaft having a proximal end, a distal end, and a shaft lumen which extends from the proximal to the distal end;
    a balloon support extending distally from the distal end of the shaft, the balloon support including a helical wire coil; and
    a flexible, inflatable tube having a proximal end in fluid communication with the shaft lumen and having a sealed distal end, the inflatable tube being wound over the helical wire coil to form a plurality of adjacent loops which, upon inflation of the tube, form a composite balloon having an outer surface for applying outward force to a vessel wall and an inner surface for defining a fluid passage through the balloon to permit perfusion while the balloon is inflated.

13. The perfusion balloon catheter of claim 12 wherein the balloon support further includes:
    retainer means for holding the inflatable tube in the helical wire coil.

14. The perfusion balloon catheter of claim 12 and further comprising:
    a guide wire external and adjacent to the shaft; and
    guide means external to and extending distally from the shaft for engaging the guide wire to permit longitudinal movement of the balloon along the guide wire.

15. The perfusion balloon catheter of claim 12 wherein the fluid passage, when the balloon is inflated, has an opening which has a cross-sectional area which is greater than about 15 percent of a total cross-sectional area of the opening and the balloon.

16. A perfusion balloon catheter comprising:
    an elongated tubular shaft having a proximal end, a distal end and an inner surface which defines a lumen from the proximal end to the distal end, the lumen further being exposed by an opening at the distal end of the shaft;
    a helical coil of flexible, inflatable tube disposed at the distal end of the tubular shaft to form an inflatable tubular-shaped balloon, the tube having a proximal end in fluid communication with the lumen and having a sealed distal end;
    a longitudinally-extending support structure through which the tube is looped to form the balloon, wherein the support structure is a coiled support member having an outer surface, a proximal end and a distal end; and
    retainer means for securing the tube to the support structure, wherein the retainer means includes a wire which extends through the coiled support member to capture loops of the tube in the coiled support member.

17. The perfusion balloon catheter of claim 16 wherein a first length of tube is inside the coiled support member.

18. The perfusion balloon catheter of claim 17 wherein the proximal end of the tube is positioned within the shaft lumen.

19. The perfusion balloon catheter of claim 18 wherein a second length of the tube extends outside of the coiled support member and is looped around the coiled support member to form a plurality of adjacent loops which cooperate to form the inflatable balloon.

20. The perfusion balloon catheter of claim 19 wherein the loops form the tubular-shaped balloon having an inner diameter which is larger than an outer diameter of the coiled support member thereby forming a perfusion passage extending from a proximal end to a distal end of the balloon.

21. The perfusion balloon catheter of claim 20 and further comprising means for connecting adjacent loops of the tubular-shaped balloon.

22. The perfusion balloon catheter of claim 20 wherein the perfusion passage has an opening, upon inflation of the balloon, with a cross-sectional area of greater than about 15 percent of a total cross-sectional area of the opening and the balloon.

23. The perfusion balloon catheter of claim 16 wherein the retainer means is positioned between each loop of the tube and an inner surface of the coiled support member.

24. The perfusion balloon catheter of claim 16 wherein the opening and the inner surface of the distal end of the tubular shaft conform to accept the outer surface of the proximal end of the coiled support member, and wherein the proximal end of the coiled support member is bonded within the distal end of the tubular shaft.

25. A rapid exchange perfusion balloon catheter for use with a guide wire, the catheter comprising:
an elongated tubular shaft having a proximal end, a distal end and a lumen extending therethrough;
a tubular-shaped balloon formed by a helical coil of flexible, inflatable tube disposed at the distal end of the tubular shaft, the tube having a proximal end in fluid communication with the distal end of the shaft and having a sealed distal end, the balloon having a perfusion passage through a central region of the helical coil;
means connected to the distal end of the shaft and extending distally of the distal end of the shaft for retaining the helical coil of flexible tube in a shape of the balloon; and
guide means external to the shaft for engaging the guide wire to permit longitudinal movement of the balloon along the guide wire, the guide means associated with the means for retaining the helical coil of flexible tube.

26. The catheter of claim 25 wherein the guide means is a tube having a proximal end, a distal end and a guide wire lumen extending therethrough.

27. The catheter of claim 25 wherein a proximal end of the flexible tube is bonded within the distal end of the tubular shaft.

28. The catheter of claim 25 wherein the means for retaining the tube includes a helical wire coil around which the tube is looped to form the balloon.

29. The catheter of claim 28 wherein the guide means is positioned within the helical wire coil.

30. The catheter of claim 25 wherein the guide means is a loop of the flexible tube positioned distally of the balloon.

31. The catheter of claim 25 wherein the perfusion passage has an opening, upon inflation of the balloon, with a cross-sectional area which is greater than about 15 percent of a total cross-sectional area of the opening and the balloon.

32. A rapid exchange perfusion balloon catheter for use with a guide wire, the catheter comprising:
an elongated tubular shaft having a proximal end, a distal end and a lumen extending therethrough;
a tubular-shaped balloon formed by a helical coil of flexible, inflatable tube disposed at the distal end of the tubular shaft, the tube having a proximal end bonded within and in fluid communication with the distal end of the shaft and having a sealed distal end, the balloon having a perfusion passage through a central region of the helical coil;
means connected to the distal end of the shaft for retaining the helical coil of flexible tube in a shape of the balloon; and
guide means external to and associated with the shaft for engaging the guide wire to permit longitudinal movement of the balloon along the guide wire, wherein the guide means is a tube having a proximal end, a distal end and a guide wire lumen extending therethrough.

33. The catheter of claim 32 wherein the means for retaining the tube includes a helical wire coil around which the tube is looped to form the balloon.

34. The catheter of claim 33 wherein the guide means is positioned within the helical wire coil.

35. The catheter of claim 32 wherein the guide means is a loop of the flexible tube positioned distally of the balloon.

36. The catheter of claim 32 wherein the perfusion passage has an opening, upon inflation of the balloon, with a cross-sectional area which is greater than about 15 percent of a total cross-sectional area of the opening and the balloon.

37. A method of sustaining an opening of a blood vessel so as to allow flow of blood through the blood vessel, the method comprising:
(a) providing a perfusion balloon which includes: an elongated tubular shaft with an inflation lumen; an open support structure which extends distally from the distal end of the shaft; and an inflatable balloon disposed at the distal end of the shaft and in fluid communication with the inflation lumen, the balloon being formed by a -flexible, inflatable tube which is looped through the support structure to form an inflatable helical coil having a perfusion passage through a central region of the helical coil;
(b) advancing the perfusion balloon catheter into the blood vessel until the balloon is positioned at a desired location within the blood vessel; and
(c) inflating the balloon so as to cause an outer composite surface of the helical coil to expand and contact a wall of the blood vessel and thereby maintain, for an extended period, a flow of blood through the perfusion passage with the balloon inflated.

38. The method of claim 37 and further comprising: positioning a second inflatable balloon within the central region of the helical coil;
inflating the second inflatable balloon to apply a radial outward force through the helical coil to the blood vessel; and
deflating the second inflatable balloon to allow blood flow through the perfusion passage.

39. The method of claim 37 wherein advancing the perfusion balloon catheter includes:
inserting a guide wire into the blood vessel; and
advancing the perfusion balloon catheter through the blood vessel along a path defined by the guide wire.

* * * * *

UNITED STATES PATENT AND TRADEMARK OFFICE
CERTIFICATE OF CORRECTION

PATENT NO. : 5,226,888
DATED : July 13, 1993
INVENTOR(S) : MICHELLE ARNEY It is certified that error appears in the above-identified patent and that said Letters Patent is hereby corrected as shown below:

On the Title Page, in the [56] References Cited section, under U.S. PATENT DOCUMENTS, insert:

5,181,911    1/1992    Shturman..........604/96

On the Title Page, in the [56] References Cited section, under U.S. PATENT DOCUMENTS, delete:

3,892,519    2/1990    Songer et al..........604/96 and insert:

4,892,519    2/1990    Songer et al..........604/96

Signed and Sealed this

Eighth Day of March, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,226,888

DATED : July 13, 1993

INVENTOR(S) : MICHELLE ARNEY

It is certified that error appears in the above-identified patent and that said Letters Patent is hereby corrected as shown below:

On the Title Page, insert: [73] Assignee:

SciMed Life Systems, Inc.

Maple Grove, Minn.

On the Title Page, in the [56] References Cited section, under U.S. PATENT DOCUMENTS, insert: 5,181,911 1/1992 Shturman........604/96

On the Title Page, in the [56] References Cited section, under U.S. PATENT DOCUMENTS, delete: 3,892,519 2/1990 Songer et al....604/96 and insert: 4,892,519 2/1990 Songer et al.......604/96

Signed and Sealed this

Twenty-eighth Day of June, 1994

*Attest:*

BRUCE LEHMAN

*Attesting Officer*    *Commissioner of Patents and Trademarks*